United States Patent
Sato

(10) Patent No.: US 10,493,626 B2
(45) Date of Patent: Dec. 3, 2019

(54) ROBOT ARM, METHOD OF ESTIMATING AMOUNT OF IRON POWDER CONTAINED IN LUBRICANT OF CONNECTING PART OF ROBOT ARM, AND ABNORMALITY SIGN DETERMINATION SYSTEM

(71) Applicant: TOYOTA JIDOSHA KABUSHIKI KAISHA, Toyota-shi, Aichi-ken (JP)

(72) Inventor: Shun Sato, Nagoya (JP)

(73) Assignee: TOYOTA JIDOSHA KABUSHIKI KAISHA, Toyota-shi, Aichi-ken (JP)

( * ) Notice: Subject to any disclaimer, the term of this patent is extended or adjusted under 35 U.S.C. 154(b) by 0 days.

(21) Appl. No.: 16/019,699

(22) Filed: Jun. 27, 2018

(65) Prior Publication Data

US 2019/0039244 A1 Feb. 7, 2019

(30) Foreign Application Priority Data

Aug. 1, 2017 (JP) .................................. 2017-149308

(51) Int. Cl.
| | |
|---|---|
| *B25J 19/02* | (2006.01) |
| *B25J 9/16* | (2006.01) |
| *B25J 9/12* | (2006.01) |
| *B25J 13/08* | (2006.01) |
| *G01N 33/28* | (2006.01) |
| *G05B 19/4062* | (2006.01) |

(52) U.S. Cl.
CPC ............. *B25J 9/1674* (2013.01); *B25J 9/126* (2013.01); *B25J 13/087* (2013.01); *G01N 33/2888* (2013.01); *G05B 19/4062* (2013.01); *G05B 2219/42271* (2013.01); *G05B 2219/42306* (2013.01)

(58) Field of Classification Search
CPC .................. H02P 21/18; G05B 19/406; G05B 2219/37525; G05B 19/0428
See application file for complete search history.

(56) References Cited

U.S. PATENT DOCUMENTS

| | | | |
|---|---|---|---|
| 2007/0277613 A1 | 12/2007 | Iwatsubo et al. | |
| 2014/0007657 A1 | 1/2014 | Matsubara et al. | |
| 2019/0061143 A1* | 2/2019 | Chandra | ................ B25J 9/0012 |

FOREIGN PATENT DOCUMENTS

| | | |
|---|---|---|
| JP | 2003-194786 A | 7/2003 |
| JP | 2004-347401 A | 12/2004 |
| JP | 2005-291738 A | 10/2005 |
| JP | 2007-248211 A | 9/2007 |

(Continued)

*Primary Examiner* — Karen Masih
(74) *Attorney, Agent, or Firm* — Sughrue Mion, PLLC

(57) ABSTRACT

An average value of differences between command current values acquired at a plurality of timings when the motor is controlled at a rotation speed within a preset fixed range in a preset period and an average value of the command current values in the period is acquired, and the average value of the differences is accumulated in an order of the acquisition. When a difference between an accumulated value of the average values of the differences up to an N−1th time and an accumulated value of the average values of the differences up to an Nth time becomes greater than or equal to a preset value, and then become less than the preset value, and then again becomes greater than or equal to the preset value, a notification of an abnormality sign in the robot arm is transmitted.

7 Claims, 8 Drawing Sheets

(56) References Cited

FOREIGN PATENT DOCUMENTS

| | | |
|---|---|---|
| JP | 2008-249549 A | 10/2008 |
| JP | 2012-078288 A | 4/2012 |
| JP | 2012-181169 A | 9/2012 |
| JP | 2013-117427 A | 6/2013 |
| JP | 2014-126463 A | 7/2014 |
| JP | 2016-020925 A | 2/2016 |
| JP | 2016-196087 A | 11/2016 |

* cited by examiner

ROBOT ARM, METHOD OF ESTIMATING AMOUNT OF IRON POWDER CONTAINED IN LUBRICANT OF CONNECTING PART OF ROBOT ARM, AND ABNORMALITY SIGN DETERMINATION SYSTEM

CROSS REFERENCE TO RELATED APPLICATIONS

This application is based upon and claims the benefit of priority from Japanese patent application No. 2017-149308, filed on Aug. 1, 2017, the disclosure of which is incorporated herein in its entirety by reference.

BACKGROUND

The present disclosure relates to a robot arm, a method of estimating an amount of iron powder contained in a lubricant of a connecting part of a robot arm, and an abnormality sign determination system.

In a common robot arm, a motor is connected to an arm with a connecting part interposed there between. The connecting part includes a lubricant such as grease inside the connecting part. An amount of the iron powder in the lubricant increases with an operation of the robot arm, and the consistency of the lubricant decreases. As a result, the lubricant deteriorates, causing an abnormality in the connecting part and eventually in the robot arm.

Commonly, for example, an abnormality sign in a robot arm is diagnosed (determined) by detecting an amount of iron powder in a lubricant using a lubricant deterioration detecting apparatus disclosed in Japanese Unexamined Patent Application Publication No. 2007-248211. In the lubricant deterioration detecting apparatus of Japanese Unexamined Patent Application Publication No. 2007-248211, the lubricant is irradiated with light from a light emitting unit, and a light receiving unit receives the light transmitted through the lubricant to calculate light transmittance of the lubricant in order to detect the amount of iron powder in the lubricant.

SUMMARY

The applicant has found the following problem. The lubricant deterioration detecting apparatus disclosed in Japanese Unexamined Patent Application Publication No. 2007-248211 requires the light emitting unit and the light receiving unit in order to detect the amount of the iron powder in the lubricant. For this reason, related art has a problem that it is costly to detect the amount of the iron powder in the lubricant or to determine the abnormality sign in the robot arm.

The present disclosure has been made in view of such a problem. An object of the present disclosure is to provide a robot arm, a method of estimating an amount of iron powder contained in a lubricant of a connecting part of a robot arm, and an abnormality sign determination system for a robot arm capable of detecting an amount of iron powder in a lubricant inexpensively or determining an abnormality sign in a robot arm.

An example aspect of the present disclosure is a robot arm including: a motor; a control unit configured to control the motor based on data indicating a command current value; an arm configured to operate based on a driving force of the motor; and a connecting part connecting the motor to the arm and including a lubricant.

An average value of differences between the command current values acquired at a plurality of timings when the motor is controlled at a rotation speed within a preset fixed range in a preset period and an average value of the command current values in the period is acquired, and the average value of the differences is accumulated in an order of the acquisition.

When a difference between an accumulated value of the average values of the differences up to an N−1th time (N is a natural number of two or greater) and an accumulated value of the average values of the differences up to an Nth time becomes greater than or equal to a preset value, and then become less than the preset value, and then again becomes greater than or equal to the preset value, a notification of an abnormality sign in the robot arm is transmitted.

In this manner, as the abnormality sign in the robot arm is determined based on the command current value, it is not necessary to use the light emitting unit and light receiving unit that are included in the lubricant deterioration detecting apparatus of the related art. Thus, the abnormality sign in the robot arm can be determined inexpensively.

An example aspect of the present disclosure is a method of estimating an amount of iron powder contained in a lubricant of a connecting part of a robot arm including a motor configured to operate based on data indicating a command current value and an arm configured to operate based on a driving force of the motor, which are connected with the connecting part interposed therebetween. The method includes:

acquiring an average value of differences between the command current values acquired at a plurality of timings when the motor is controlled at a rotation speed within a preset fixed range in a preset first period and an average value of the command current values in the first period, and accumulating the average values of the differences in an order of the acquisition; and estimating the amount of iron powder based on a product of an accumulated value of the average values of the differences and a preset coefficient.

In this manner, as the amount of iron powder in the lubricant is estimated based on the command current value, it is not necessary to use the light emitting unit and light receiving unit that are included in the lubricant deterioration detecting apparatus of the related art. Thus, the amount of iron powder in the lubricant can be estimated inexpensively.

In the above method of estimating an amount of iron powder contained in a lubricant of a connecting part of a robot arm, the preset coefficient is preferably a value obtained by dividing a measured amount of the iron powder contained in the lubricant when the robot arm is operated for the second period by the accumulated value of the average values of the differences in a preset second period.

In the above method of estimating an amount of iron powder contained in a lubricant of a connecting part of a robot arm, the second period is preferably a period, when a difference between the accumulated value of the average values of the differences up to an N−1th time (N is a natural number of two or greater) and the accumulated value of the average values of the differences at an Nth time becomes less than a preset value, from when the average value of the differences is acquired for the first time until when the average value of the differences at the Nth time is acquired.

According to another example aspect of the present disclosure, an abnormality sign determination system of a robot arm includes:

a motor;

a control unit configured to control the motor based on data indicating a command current value;

an arm configured to operate based on a driving force of the motor, a connecting part connecting the motor to the arm and including a lubricant; and a server communicably connected to the robot arm.

The control unit acquires an average value of differences between the command current values acquired at a plurality of timings when the motor is controlled at a rotation speed within a preset fixed range in a preset period and an average value of the command current values in the period, and transmits data indicating the average value of the differences to the server.

The server accumulates the average values of the differences in an order in which the control unit acquires the average value of the differences, and when a difference between an accumulated value of the average values of the differences up to an N−1th time (N is a natural number of two or greater) and an accumulated value of the average values of the differences up to an Nth time becomes greater than or equal to a preset value, and then become less than the preset value, and then again becomes greater than or equal to the preset value, the server determines that there is an abnormality sign in the robot arm.

In this manner, as the abnormality sign in the robot arm is determined based on the command current value, it is not necessary to use the light emitting unit and light receiving unit that are included in the lubricant deterioration detecting apparatus of the related art. Thus, the abnormality sign in the robot arm can be determined inexpensively.

Another example aspect of the present disclosure is an abnormality sign determination system of a robot arm including:

a motor;

a control unit configured to control the motor based on data indicating a command current value;

an arm configured to operate based on a driving force of the motor, a connecting part connecting the motor to the arm and including a lubricant; and a first server communicably connected to the robot arm.

The control unit acquires, every time the lubricant is replaced, an average value of differences between the command current values acquired at a plurality of timings when the motor is controlled at a rotation speed within a preset fixed range in a preset period and an average value of the command current values in the period, and transmits data indicating the average value of the differences to the first server.

The first server accumulates the average values of the differences in an order in which the robot arm acquires the average value of the differences, and when a difference between an accumulated value of the average values of the differences for a first lubricant and an accumulated value of the average values of the differences for a replaced lubricant becomes greater than or equal to a preset value at a point when periods since the first lubricant and the replaced lubricant are started to be used become equal, the first server determines that there is an abnormality sign in the robot arm.

In this manner, as the abnormality sign in the robot arm is determined based on the command current value, it is not necessary to use the light emitting unit and light receiving unit that are included in the lubricant deterioration detecting apparatus of the related art. Thus, the abnormality sign in the robot arm can be determined inexpensively.

In the above abnormality sign determination system of a robot arm, the first server preferably transmits data indicating the accumulated value of the average values of the differences for the replaced lubricant excluding the accumulated values of the average values of the differences for the first lubricant and for a lubricant in use to a second server and deletes the data from the first server.

According to the present disclosure, it is possible to inexpensively detect an amount of iron powder in a lubricant or determine an abnormality sign in a robot arm.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

Hereinafter, specific embodiments to which the present disclosure is applied will be described in detail with reference to the drawings. However, the present disclosure is not limited to the following embodiments. Further, the following descriptions and drawings are simplified as appropriate for clarity of the descriptions.

<First Embodiment>

Figure 1:
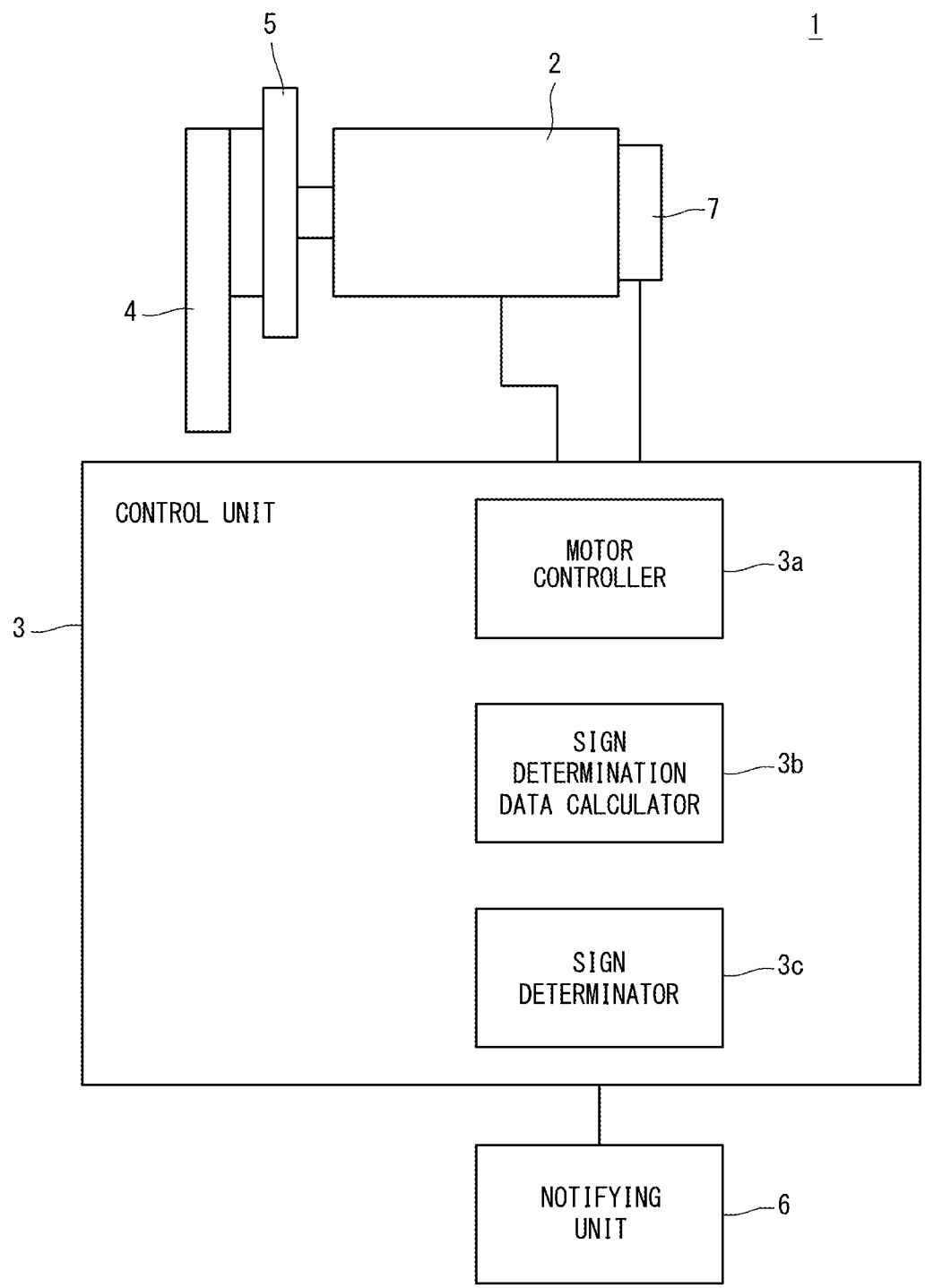
FIG. 1 is a view schematically showing a configuration of a robot arm according to a first embodiment.

First, a configuration of a robot arm according to this embodiment will be briefly described. FIG. 1 is a view schematically showing a configuration of a robot arm according to this embodiment. The robot arm 1 includes a motor 2, a control unit 3, an arm 4, a connecting part 5, and a notifying unit 6. The robot arm 1 performs a repetitive operation on, for example, a production line.

The motor 2 includes an encoder 7. The encoder 7 outputs data indicating a rotation angle or rotation angular speed of the motor 2 to the control unit 3. The control unit 3 includes a motor controller 3a, a sign determination data calculator 3b, and a sign determinator 3c. The motor controller 3a controls the motor 2 based on data indicating a command current value so that the arm 4 executes the preset repetitive operation.

Specifically, the motor controller 3a generates a command current value based on data indicating a rotation angle or a rotation angular speed of the motor 2, which is input from the encoder 7, and controls the motor 2 based on data indicating the generated command current value so that the motor 2 rotates at a preset rotation angle and the arm 4 executes a preset repetitive operation. The motor controller 3a can control the motor 2 by, for example, PID (Proportional-Integral-Differential), ID control, and PD control.

The sign determination data calculator 3b acquires an average value of differences between the command current values acquired at a plurality of timings when the motor 2 is controlled at a rotation speed within a preset fixed range in a preset period and an average value of the command current values in this period, and then outputs data indicating the acquired average value of the differences to the sign determinator 3c. The details of this operation will be described later.

The sign determinator 3c accumulates the average values of the differences indicated by the data input from the sign determination data calculator 3b, and determines an abnormality sign in the robot arm 1 based on an accumulated value of the average values of the differences. The details of this operation will be described later.

The arm 4 includes an arm part and a hand part. One end of the arm part is connected to the motor 2 with the connecting part 5 interposed therebetween, and the hand part is provided at the other end of the arm part. The details of the arm 4 are not shown in the drawings.

The connecting part 5 is a speed reducer that connects the motor 2 to the arm 4. A lubricant such as grease is sealed inside the connecting part 5. However, the connecting part 5 is not limited to a speed reducer and may be a drive transmission gear. The lubricant does not need to be sealed inside the connecting part 5 and instead may be present between the gears of the connecting part 5.

The notifying unit 6 notifies the outside of the abnormality sign in the robot arm 1. The notifying unit 6 may be a display device that can make a visual notification to the outside or a speaker that can make an audio notification to the outside. However, the notifying unit 6 may be any means as long as it can notify the outside of an abnormality sign in the robot arm 1.

Figure 2:
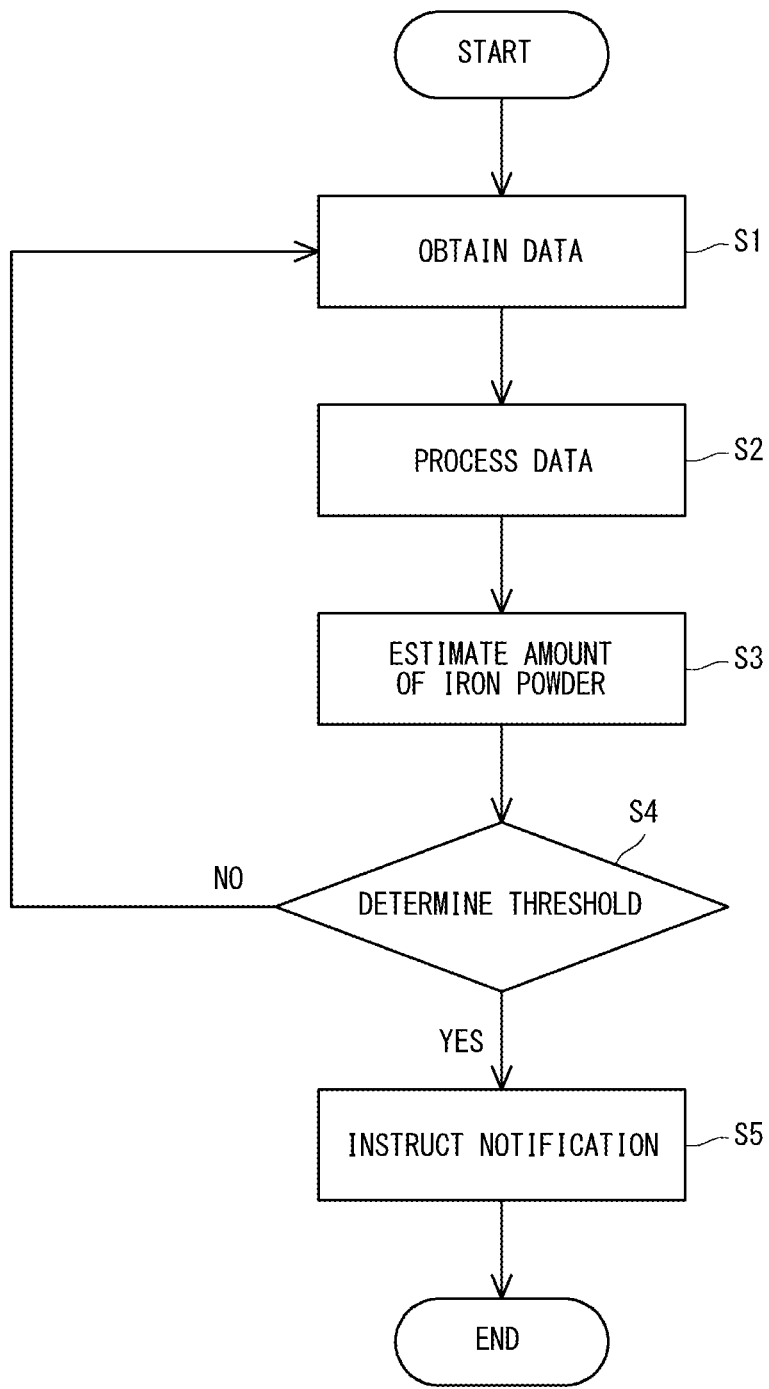
FIG. 2 is a flowchart showing a flow for determining an abnormality sign in the robot arm according to the first embodiment.
Figure 3:
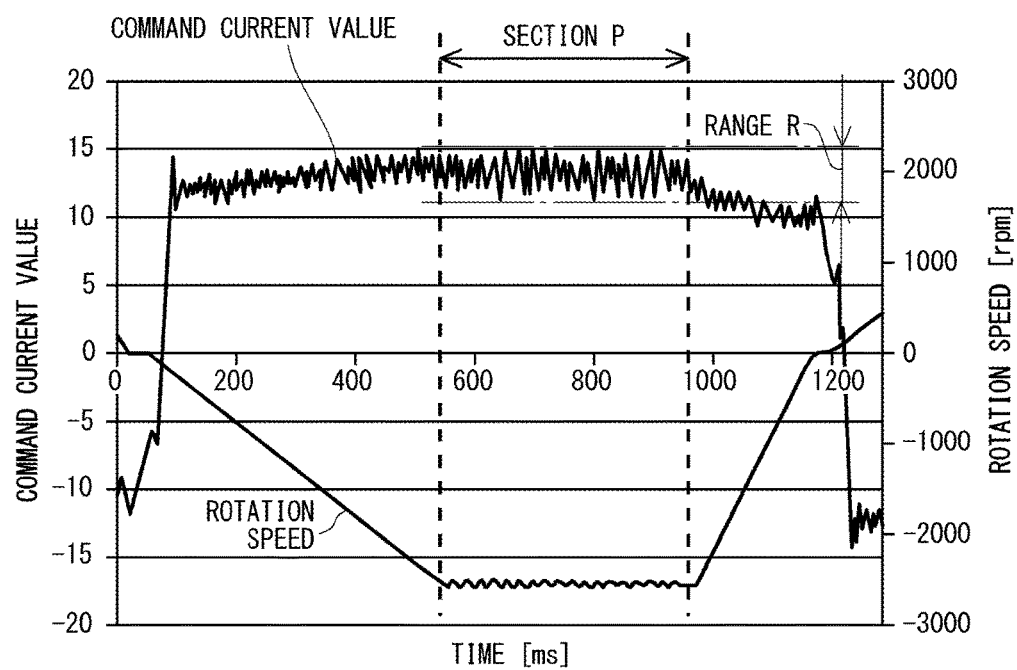
FIG. 3 is a view showing a relationship between a command current value and a rotation speed of a motor.
Figure 4:
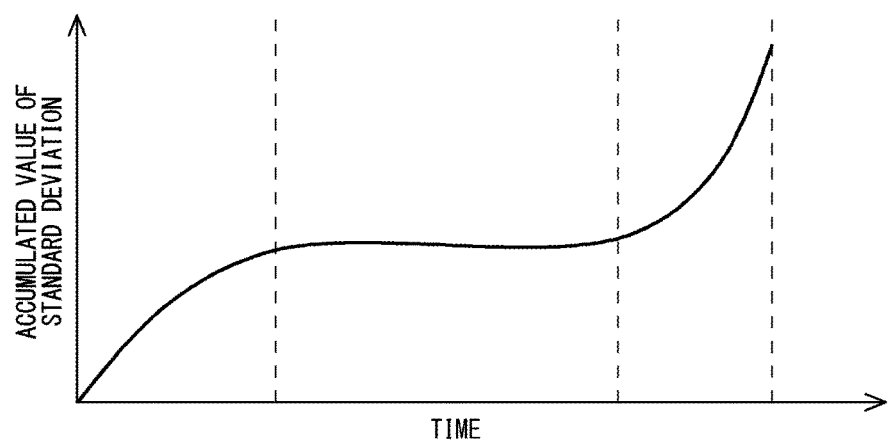
FIG. 4 is a view showing a relationship between an accumulated value of standard deviations and time.

Next, a flow for determining the abnormality sign in the robot arm 1 according to this embodiment will be described. FIG. 2 is a flowchart showing a flow for determining an abnormality sign in the robot arm according to this embodiment. FIG. 3 is a view showing a relationship between the command current value and the rotation speed of the motor. FIG. 4 is a view showing a relationship between the accumulated value of the standard deviations and time.

In this embodiment, the abnormality sign in the robot arm 1 is determined while the robot arm 1 is operated normally. Thus, as described above, the motor controller 3a generates the command current value based on the data indicating the rotation angle or the rotation angular speed of the motor 2 (i.e., the rotation speed of the motor 2), which is input from the encoder 7, and controls the motor 2 based on the data indicating the generated command current value so that the motor 2 rotates at the preset rotation angle and the arm 4 executes the preset repetitive operation.

At this time, the command current value and the rotation speed of the motor 2 appear as shown in FIG. 3. The data indicating the command current value is generated in such a way that a waveform indicating the rotation speed of the motor 2 repeatedly appears to cause the arm 4 to execute the repetitive operation as described above. As shown in FIG. 3, the rotation speed of the motor 2 has a section P that falls within a preset fixed range R in a preset period. The section P appears in every repetitive operation of the arm 4.

On the other hand, as shown in FIG. 2, to the sign determination data calculator 3b, the data indicating the rotation speed of the motor 2 is input from the encoder 7, and the data indicating the command current value is input from the motor controller 3a (S1).

Next, the sign determination data calculator 3b acquires an average value of differences between the command current values acquired at a plurality of timings when the motor 2 is controlled at the rotation speed within a preset fixed range R in the preset period, i.e., within the above-described section P, and an average value of the command current values in the section P. The sign determination data calculator 3b extracts, for example, the command current values at peaks and troughs in the respective waveforms indicating the command current values in the section P as the command current values acquired at the plurality of timings in the section P. However, the timings to extract the command current values may be preset fixed timings, and are not limited in particular.

The sign determination data calculator 3b according to this embodiment estimates the section P based on the rotation speed of the motor 2 indicated by the data input from the encoder 7. Then, the sign determination data calculator 3b calculates a standard deviation of the command current value in the estimated section P, and outputs data indicating the calculated standard deviation to the sign determinator 3c (S2).

However, the sign determination data calculator 3b may estimate the timing at which the section P appears on the waveform indicating the command current value based on, for example, a timer. Further, the sign determination data calculator 3b may calculate an average deviation of the command current values in the section P.

Next, the sign determinator 3c estimates the amount of iron powder contained in the lubricant (S3). The applicant has found that an accumulated value of the standard deviations also appears in a linear curve as the amount of iron powder contained in the lubricant increases. That is, the applicant has found that there is a predetermined correlation between the amount of iron powder contained in the lubricant and the accumulated value of the standard deviations.

Therefore, the sign determinator 3c accumulates the standard deviation indicated by the input data in an order in which the data is input (which is, the order in which the sign determination data calculator 3b calculates the standard deviation). That is, the sign determinator 3c calculates the accumulated value of the standard deviation according to the following <Equation 1>.

$$H_N = H_{N-1} + (S_{N-1} - S_N) \qquad \text{<Equation 1>}$$

In Equation 1, H is the accumulated value of the standard deviations, N is the number of occurrences of the section P since the lubricant is started to be used, and S is the standard deviation.

Next, the sign determinator 3c estimates the amount of iron powder contained in the lubricant based on the following <Equation 2>.

$$\rho = \alpha \times H_N \qquad \text{<Equation 2>}$$

In Equation 2, $\alpha$ is a conversion coefficient, and $\rho$ is an estimated amount of iron powder.

At this time, α can be calculated by, for example, the following <Equation 3>.

$$\alpha = \rho_{rD}/H_D$$ <Equation 3>

In Equation 3, D is the number of days passed since the date on which the lubricant is started to be used, $\rho_{rD}$ is the measured value of the amount of iron powder contained in the lubricant on the date corresponding to the number of days passed since the date on which the lubricant is started to be used.

As shown in FIG. 4, the accumulated value H sharply rises due to removal of burrs from the gear and the like of the connecting part 5. Then, the increase of the accumulated value H is stabilized as the removal of burrs from the gear and the like comes close to an end. The accumulated value H sharply rises again when the surface treatment of the gear and the like of the connecting part 5 peels off, and the gear and the like continue to wear out.

The period during which the accumulated value H sharply rises does not represent the original property of the lubricant, and instead the period during which the increase of the accumulated value H is stabilized represents the original property of the lubricant. Therefore, in this embodiment, the date including a first point when the increase of the accumulated value H is stabilized after the period in which the accumulated value H sharply rises for the first time is set as a reference day (e.g., 180 days), and a conversion coefficient α is calculated. Alternatively, instead of using the number of days as a reference, the conversion coefficient α may be calculated with reference to the acquisition time of the Nth standard deviation when a difference between the accumulated value $H_{N-1}$ and the accumulated value $H_N$ becomes less than a preset first threshold.

Next, the sign determinator 3c determines whether the estimated amount of iron powder ρ is equal to or greater than a preset second threshold (S4). When the estimated amount of iron powder ρ is greater than or equal to the second threshold value (YES in S4), the sign determinator 3c determines that there is a sign of an abnormality in the robot arm 1, because the lubricant is deteriorated. Then, the sign determinator 3c generates command data for notifying the outside of an abnormality sign in the robot arm 1, and outputs the command data to the notifying unit 6 (S5). When the command data is input, the notifying unit 6 notifies the outside of the abnormality sign in the robot arm 1. That is, the notifying unit 6 encourages the replacement of the lubricant.

On the other hand, when the estimated amount of iron powder ρ is less than the second threshold (NO in S4), the sign determinator 3c determines that there is no sign of an abnormality in the robot arm 1 and outputs, to the sign determination data calculator 3b, the command data indicating that the data is continuously acquired. After that, the process returns to Step S1. That is, the amount of iron powder is estimated based on the accumulated value $H_{N+1}$ of the (N+1)th standard deviation, and the process transitions to the process for determining whether the estimated amount of iron powder ρ is greater than or equal to the second threshold.

As described above, in this embodiment, the amount of iron powder contained in the lubricant is estimated based on the command current value. Thus, even without the light emitting unit or the light receiving unit that are included in the lubricant deterioration detecting apparatus of the related art, this embodiment enables the amount of iron powder in the lubricant to be determined, which enables the deterioration of the lubricant to be determined based on the amount of iron powder, and eventually an abnormality sign in the robot arm 1 to be determined. Accordingly, the robot arm 1 and the method of estimating the amount of iron powder according to this embodiment can inexpensively determine the amount of iron powder in the lubricant and the abnormality sign in the robot arm 1.

Moreover, this embodiment enables the amount of iron powder contained in the lubricant to be estimated without collecting the lubricant from the connecting part 5. In this respect, this embodiment is suitable for a robot arm using the connecting part 5 with the lubricant sealed therein. Additionally, this embodiment can omit the operation of collecting the lubricant from the connecting part 5.

The robot arm 1 and the method of estimating the amount of iron powder according to this embodiment can constantly monitor the amount of iron powder contained in the lubricant based on the command current value. That is, the robot arm 1 does not has to be stopped to estimate the amount of iron powder contained in the lubricant.

Figure 5:
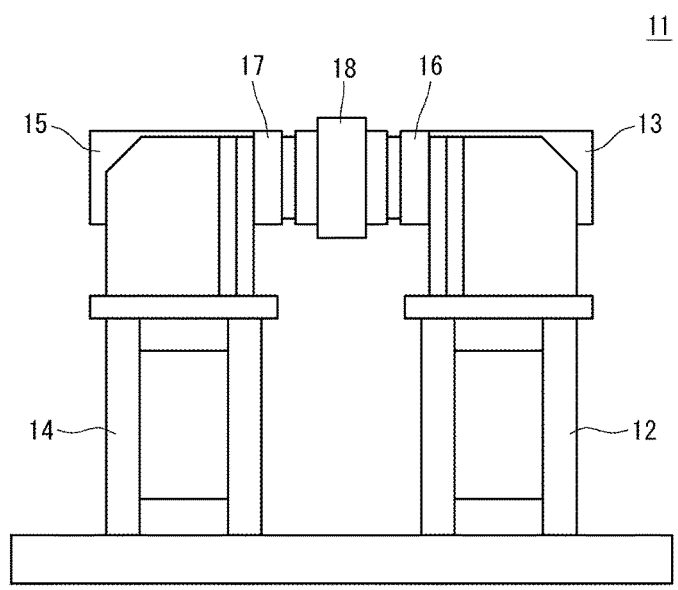
FIG. 5 is a view schematically showing a durability test apparatus of a speed reducer.
Figure 6:
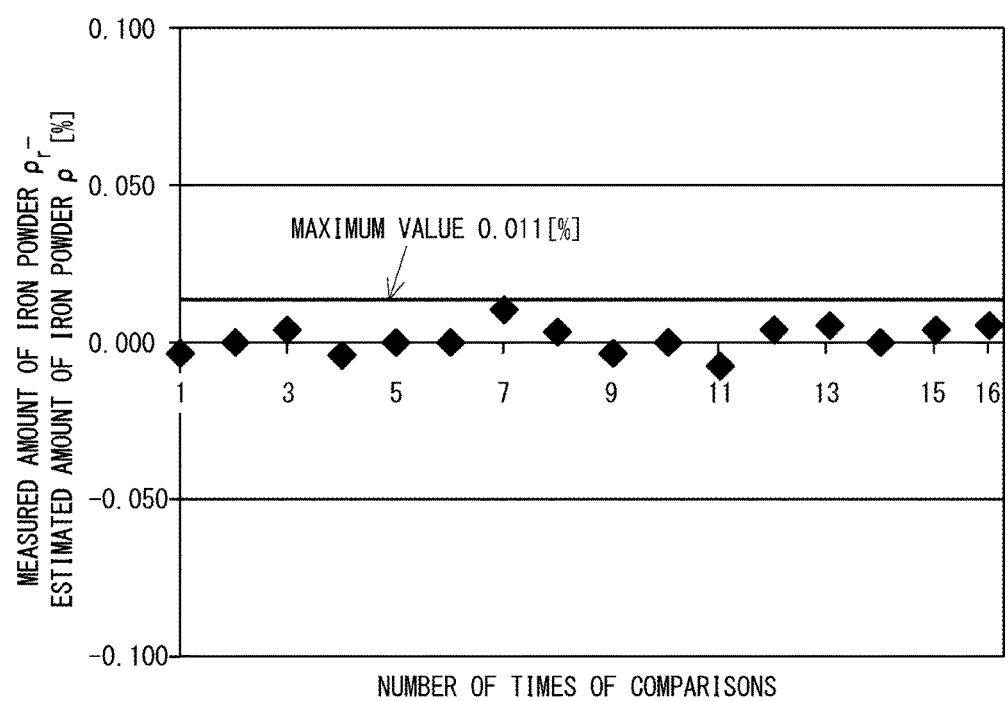
FIG. 6 is a view showing a relationship between a difference between a measured amount of iron powder and an estimated amount of iron powder and the number of times of comparisons.

The applicant has found, in a manner described below, a difference between the amount of iron powder (the measured amount of iron powder) $\rho_r$ actually contained in the lubricant and the amount of iron powder (the estimated amount of iron powder) ρ estimated as described above. FIG. 5 is a view schematically showing a durability test apparatus of the speed reducer. FIG. 6 is a view showing a relationship between a difference of the measured amount of iron powder and the estimated amount of iron powder and the number of times of comparisons.

As shown in FIG. 5, the durability test apparatus 11 includes a first motor 13 supported by a first jig 12 and a second motor 15 supported by a second jig 14. An output shaft of the first motor 13 is connected to an input part of a first speed reducer 16, and an output shaft of the second motor 15 is connected to an input part of a second speed reducer 17. An output part of the first speed reducer 16 and an output part of the second speed reducer 17 are connected with a coupling 18 interposed therebetween.

Such a durability test apparatus 11 was used to rotate the first motor 13 while a load is applied by the second motor 15 and measure the amount of iron powder $\rho_r$ in the lubricant inside the first speed reducer 16 every half a year a total of 16 times (i.e., a test period corresponding to eight years). Then, a difference between the amount of iron powder $\rho_r$ and the estimated amount of iron powder ρ was checked. During the test period, the lubricant was not replaced. The standard deviations S were continuously accumulated in the test period corresponding to eight years, and the amount of iron powder was estimated based on the accumulated value H every half a year.

As a result, as shown in FIG. 6, in the comparison between the measured amount of iron powder $\rho_r$ measured 16 times and the estimated amount of iron powder ρ estimated 16 times, a maximum difference between the measured amount of iron powder $\rho_r$ and the estimated amount of iron powder ρ necessary for knowing when to carry out the lubricant inspection and lubricant replacement is the resolution 0.05% or less. This indicate that the amount of iron powder ρ estimated by the above <Equation 2> is highly accurate.

<Second Embodiment>

In the first embodiment, the abnormality sign in the robot arm 1 is determined based on the estimated amount of iron powder ρ estimated based on the accumulated value H of the standard deviation. However, the abnormality sign in the robot arm 1 may be determined directly from the accumulated value H of the standard deviation.

As shown in FIG. 4, the accumulated value H sharply rises due to removal of burrs from the gear and the like of the connecting part 5. Then, the increase of the accumulated value H is stabilized as the removal of burrs from the gear and the like comes close to an end. The accumulated value H sharply rises again when the surface treatment of the gear and the like of the connecting part 5 peels off, and the gear and the like continue to wear out.

Therefore, the sign determinator 3c according to this embodiment determines whether a difference between the accumulated value $H_{N-1}$ up to the (N-1)th time and the accumulated value $H_N$ up to the Nth time (i.e., the amount of change) becomes greater than or equal to a preset third threshold, and then becomes less than the third threshold, and then again becomes greater than or equal to the third threshold. In other words, it is determined whether an inclination of a straight line connecting the accumulated value $H_{N-1}$ to the accumulated value $H_N$ becomes greater than or equal to a preset inclination.

When the difference between the accumulated value $H_{N-1}$ and the accumulated value $H_N$ becomes greater than or equal to the third threshold, and then becomes less than the third threshold, and then again becomes greater than or equal to the third threshold, the sign determinator 3c determines that there is an abnormality sign in the robot arm 1. This is because when the difference between the accumulated value $H_{N-1}$ and the accumulated value $H_N$ becomes greater than or equal to the third threshold, and then becomes less than the third threshold, and then again becomes greater than or equal to the third threshold, it can be assumed that, for example, the surface treatment of the gear and the like of the connecting part 5 is peeling off, and deterioration of the lubricant is progressing.

In this way, deterioration of the lubricant and eventually an abnormality sign in the robot arm 1 can be easily determined using the correlation between the amount of iron powder contained in the lubricant and accumulated value H of the standard deviation, which has been found by the applicant.

<Third Embodiment>

Figure 7:
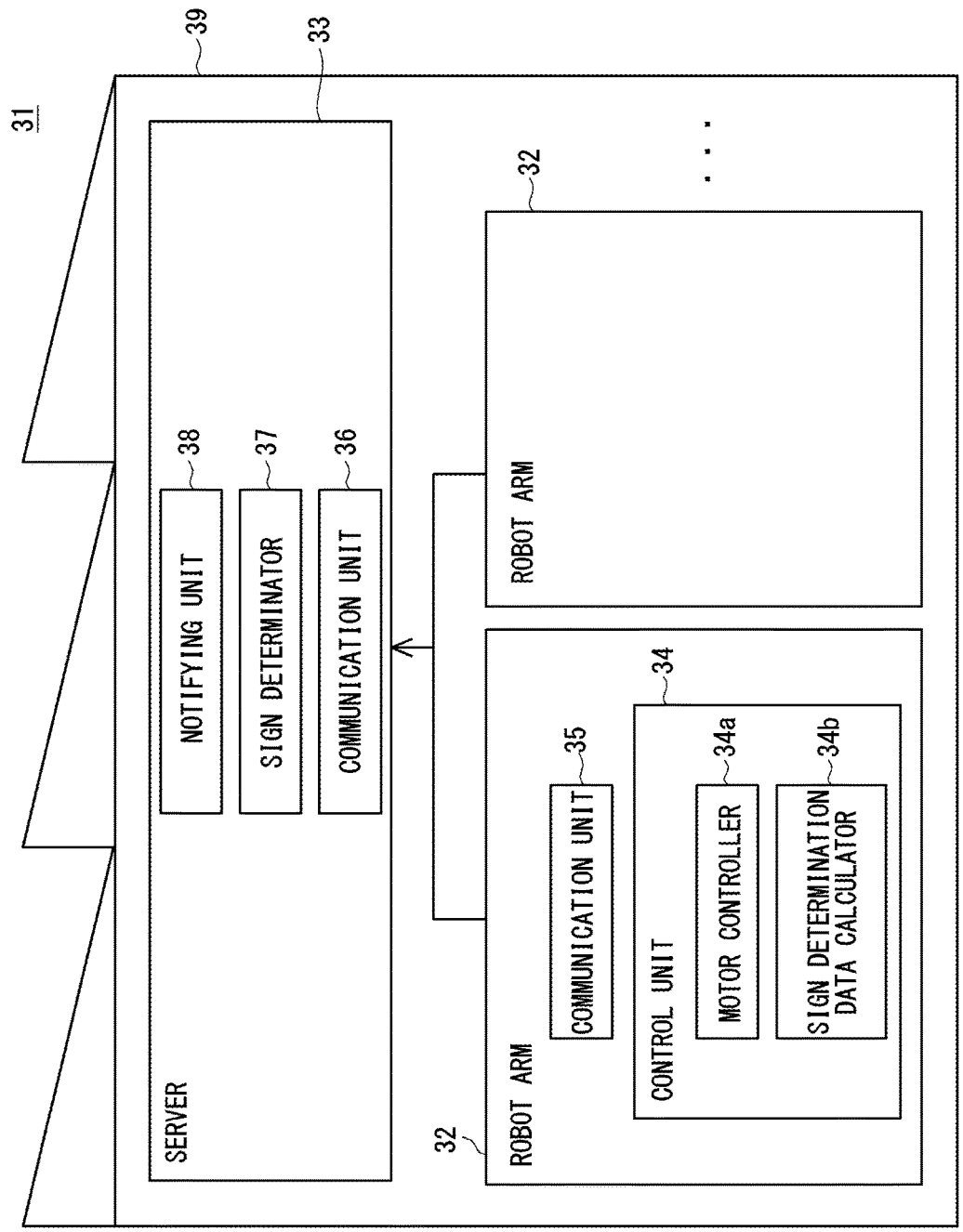
FIG. 7 is a view schematically showing an abnormality sign determination system of a robot arm according to a third embodiment.

In the first embodiment, the sign determinator 3c of the control unit 3 included in the robot arm 1 causes the processing such as the estimation of the amount of iron powder and determination of the abnormality sign in the robot arm 1 to be executed. However, the processing may be executed by a server. FIG. 7 is a view schematically showing an abnormality sign determination system of the robot arm according to this embodiment.

As shown in FIG. 7, an abnormality sign determination system 31 of the robot arm according to this embodiment includes a plurality of robot arms 32 and a server 33. Each of the robot arms 32 has substantially the same configuration as that of the robot arm 1 of the first embodiment. Specifically, the controller 34 includes a motor controller 34a and a sign determination data calculator 34b corresponding to the motor controller 3a and the sign determination data calculator 3b of the control unit 3 according to the first embodiment, respectively. However, the robot arm 32 does not include the sign determinator 3c of the control unit 3 and the notifying unit 6 included in the robot arm 1 of the first embodiment. The robot arm 32 includes a communication unit 35 that establishes communication with the server 33. The robot arm 32 transmits data indicating a standard deviation S calculated by the sign determination data calculator 34b to the server 33 via the communication unit 35.

For example, communication means between the robot arm 32 and the server 33 may be communication means such as an internet line.

The server 33 includes a communication unit 36, a sign determinator 37 corresponding to the sign determinator 3c of the control unit 3 of the first embodiment, and a notifying unit 38. The server 33 is installed, for example, inside a facility 39 such as a factory. The sign determinator 37 calculates the accumulated value H based on the standard deviation S indicated by the data received from the robot arm 32 via the communication unit 36, and estimates the amount of iron powder based on the calculated accumulated value H. Then the sign determinator 37 determines an abnormality sign in the robot arm 32 based on the estimated amount of iron powder ρ. When the sign determinator 37 determines that there is an abnormality sign in the robot arm 32, it causes the notifying unit 38 to notify the outside of the abnormality sign in the robot arm 32.

As described above, the abnormality sign determination system 31 of the robot arm 32 according to this embodiment causes the server 33 to process the estimation of the amount of iron powder and the determination of the abnormality sign in the robot arm 32. This reduces the processing load of the control unit 34 of the robot arm 32. Like the second embodiment, the abnormality sign in the robot arm 32 may be determined directly from the accumulated value H.

Command data for the server 33 to notify the outside of the abnormality sign in the robot arm 32 may be transmitted to a terminal device possessed by an operator via the communication means such as an internet line. Then, the terminal device may notify the outside of the abnormality sign in the robot arm 32.

<Fourth Embodiment>

Figure 8:
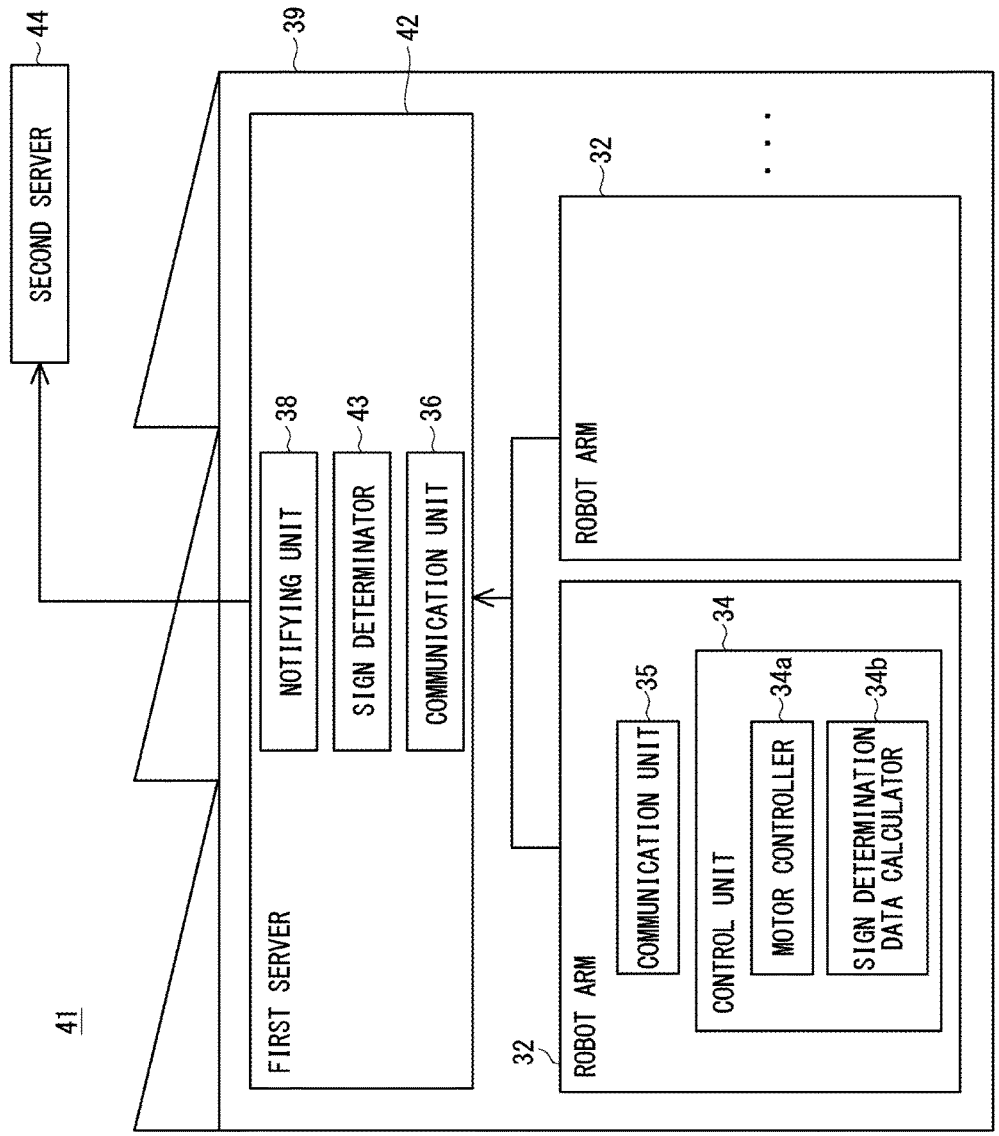
FIG. 8 is a view schematically showing an abnormality sign determination system of a robot arm according to a fourth embodiment.
Figure 9:
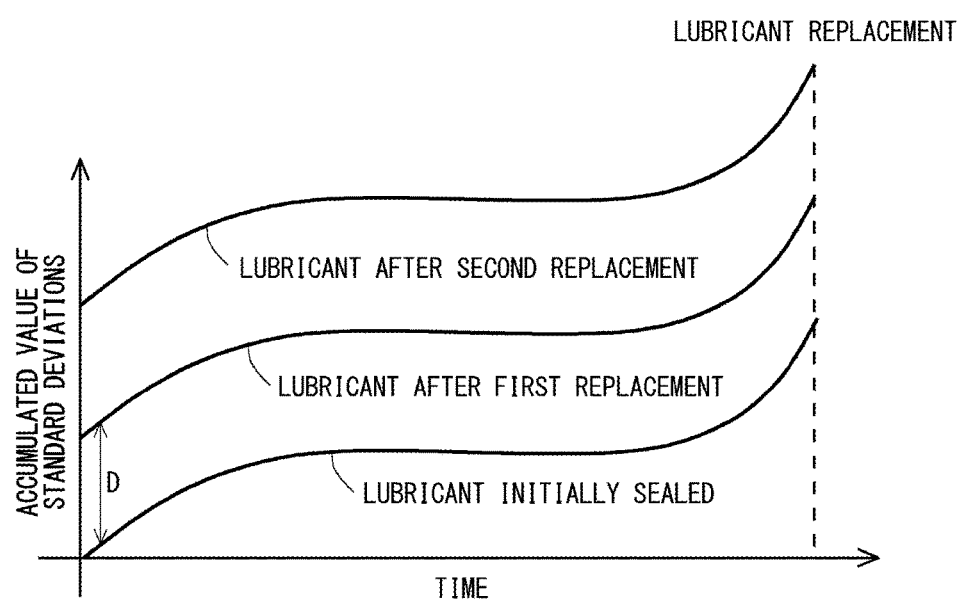
FIG. 9 is a view showing a relationship between an accumulated value of standard deviations of a lubricant initially sealed in a connecting part, an accumulated value of standard deviations of a lubricant after first replacement, and an accumulated value of standard deviations of a lubricant after second replacement and time.

An abnormality sign determination system of a robot arm according to this embodiment determines an abnormality sign in a robot arm based on an increase in an accumulated value H caused by wearing-out of a gear and the like that is already occurring in a connecting part after a lubricant in the connecting part is replaced. FIG. 8 is a view schematically showing the abnormality sign determination system of the robot arm according to this embodiment. FIG. 9 is a view showing a relationship between an accumulated value of standard deviations of a lubricant initially sealed in a connecting part, an accumulated value of standard deviations of a lubricant after first replacement, an accumulated value of standard deviations of a lubricant after second replacement and time. Note that the descriptions overlapping with those in the third embodiment will be omitted, and the same reference numerals will be used for the same elements.

As shown in FIG. 8, an abnormality sign determination system 41 of the robot arm according to this embodiment has substantially the same configuration as that of the abnormality sign determination system 31 of the robot arm 32 according to the third embodiment. However, in the abnormality sign determination system 41, details of processing of a sign determinator 43 of a first server 42 differs from that of the abnormality sign determination system 31.

When the amount of the iron powder in the lubricant in the connecting part 5 increases, and the lubricant is replaced, the gear and the like of the connecting part 5 have already worn out. As shown in FIG. 9, even immediately after the replacement of the lubricant, the replaced lubricant contains iron powder due to the wearing-out of the gear and the like. Thus, the accumulated value H for the replaced lubricant indicates a high value as compared with the accumulated value H of the lubricant before replacement. When a difference D between the accumulated value H for the first lubricant and the accumulated value H for the replaced lubricant becomes greater than or equal to a preset fourth threshold at a point when periods since these lubricants are started to be used become equal, it can be estimated that the gear and the like of the connecting part 5 have already worn out.

Therefore, when the difference D between the accumulated value H for the first lubricant and the accumulated value H for the replaced lubricant is greater than or equal to the fourth threshold at a point when the periods since the lubricants are started to be used become equal, the sign determinator 43 according to this embodiment determines that there is an abnormality sign in the robot arm 32.

In the above-described first to third embodiments, the deterioration of the lubricant is determined based on the amount of change in the accumulated value H for the lubricant in use. For this reason, it is not possible to estimate how much the gear and the like have worn out with the replaced lubricant in comparison to the wearing-out of the gear and the like with the first lubricant. On the other hand, this embodiment makes it possible to continuously estimate how much the gear and the like of the connecting part 5 have worn out even after the lubricant is replaced by calculating the difference between the accumulated value H for the first lubricant and the accumulated value H for the replaced lubricant. This enables an abnormality sign in the robot arm 32 caused by the wearing-out of the gear and the like to be determined.

The first server 42 may store data of the accumulated values H for all the lubricants. In such a case, the data indicating the accumulated values H for the replaced lubricant excluding the accumulated values H for the first lubricant and the lubricant in use may be transmitted to a second server 44, and this data in the first server 42 may be deleted. The second server 44 is installed outside the facility 39 and is connected to the first server 42 via communication means such as an internet line. This makes it possible to refer to the accumulated values H of the lubricants exchanged in the past when the connecting part 5 fails. In addition, the load on the first server 42 can be reduced as compared with the case when all the accumulated values H for the lubricants exchanged in the past are stored in the first server 42.

The present disclosure is not limited to the above-described embodiments, and can be appropriately changed without departing from the spirit of the disclosure.

In the above embodiments, the present disclosure has been described as a hardware configuration, but the present disclosure is not limited to this. The present disclosure can be implemented by causing a CPU (Central Processing Unit) to execute a computer program that performs specified processing.

The program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A robot arm comprising:
a motor;
a controller configured to control the motor based on data indicating at least one command current value;
an arm configured to operate based on a driving force of the motor; and
a connecting part connecting the motor to the arm and including a lubricant,
wherein the controller is further configured to:
perform an acquisition to acquire command current values at a plurality of timings when the motor is controlled at a rotation speed within a preset fixed range, in a preset time period,
perform a determination to determine an average value of differences between the command current values and an average value of the command current values in the preset time period, and
repeat the acquisition and the determination in a second preset time period and accumulate average values of the differences in a sequential order of each determination,
transmit a notification of an abnormality sign in the robot arm to a display or speaker, when a difference between an accumulated value of the average values of the differences up to an N−1th time (wherein N is a natural number of two or greater) and an accumulated value of the average values of the differences up to an Nth time becomes greater than or equal to a preset value, and then become less than the preset value, and then again becomes greater than or equal to the preset value.

2. A method of estimating an amount of iron powder contained in a lubricant of a connecting part of a robot arm, the robot arm comprising a motor configured to operate based on data indicating at least one command current value and an arm configured to operate based on a driving force of the motor, the motor and the arm being connected with the connecting part interposed therebetween, the method comprising:
acquiring command current values at a plurality of timings when the motor is controlled at a rotation speed within a preset fixed range, in a preset first time period,
determining an average value of differences between the command current values and an average value of the command current values in the preset first time period, and
repeating the acquiring and the determining in an additional preset time period, and accumulating average values of the differences in a sequential order of each determining; and
estimating the amount of the iron powder based on a product of an accumulated value of the average values of the differences and a preset coefficient.

3. The method according to claim 2, wherein the preset coefficient is a value obtained by dividing a measured amount of the iron powder contained in the lubricant when the robot arm is operated for a second time period by the accumulated value of the average values of the differences in a preset second time period.

4. The method according to claim 3, wherein the second time period is a time period, when a difference between the accumulated value of the average values of the differences up to an N−1th time (wherein N is a natural number of two or greater) and the accumulated value of the average values of the differences at an Nth time becomes less than a preset value, from when the average value of the differences is acquired for the first time until when the average value of the differences at the Nth time is acquired.

5. An abnormality sign determination system of a robot arm comprising:
a motor;
a controller configured to control the motor based on data indicating at least one command current value;
an arm configured to operate based on a driving force of the motor;
a connecting part connecting the motor to the arm and including a lubricant; and
a server communicably connected to the robot arm, wherein
the controller is further configured to:
    perform an acquisition to acquire command current values at a plurality of timings when the motor is controlled at a rotation speed within a preset fixed range, in a preset time period,
    perform a determination to determine an average value of differences between the command current values and an average value of the command current values in the preset time period,
    perform a transmission to transmit data indicating the average value of the differences to the server, and
    repeat the acquisition and the determination in a second preset time period,
wherein the server receives a plurality of average values of the differences and accumulates the plurality of average values of the differences in an order in which the controller determines average values of the differences, and when a difference between an accumulated value of the average values of the differences up to an N−1th time (wherein N is a natural number of two or greater) and an accumulated value of the average values of the differences up to an Nth time becomes greater than or equal to a preset value, and then become less than the preset value, and then again becomes greater than or equal to the preset value, the server determines that there is an abnormality sign in the robot arm.

6. An abnormality sign determination system of a robot arm comprising:
a motor;
a controller configured to control the motor based on data indicating at least one command current value;
an arm configured to operate based on a driving force of the motor;
a connecting part connecting the motor to the arm and including a lubricant; and
a first server communicably connected to the robot arm, wherein
the controller is further configured to, every time the lubricant is replaced:
    perform an acquisition to acquire command current values at a plurality of timings when the motor is controlled at a rotation speed within a preset fixed range in a preset time period,
    perform a determination to determine an average value of differences between the command current values and an average value of the command current values in the preset time period,
    perform a transmission to transmit data indicating the average value of the differences to the first server, and
    repeat the acquisition and the determination in a second preset time period,
wherein the first server receives a plurality of average values of the differences and accumulates the plurality of average values of the differences in an order in which the robot arm determines average values of the differences, and when a difference between an accumulated value of the average values of the differences for a first lubricant and an accumulated value of the average values of the differences for a replaced lubricant becomes greater than or equal to a preset value at a point when periods since the first lubricant and the replaced lubricant are started to be used become equal, the first server determines that there is an abnormality sign in the robot arm.

7. The abnormality sign determination system of a robot arm according to claim 6, wherein the first server transmits data indicating the accumulated value of the plurality of average values of the differences for the replaced lubricant, excluding the accumulated values of the average values of the differences for the first lubricant and for a lubricant in use, to a second server, and
the first server deletes the data from the first server.

* * * * *